United States Patent
Wang et al.

(10) Patent No.: US 11,905,235 B2
(45) Date of Patent: Feb. 20, 2024

(54) METHOD FOR PREPARING 2,2-BIS(4-HYDROXYCYCLOHEXYL)PROPANE

(71) Applicant: CHINA PETROCHEMICAL DEVELOPMENT CORPORATION, TAIPEI (TAIWAN), Kaohsiung (TW)

(72) Inventors: Yi-Chi Wang, Kaohsiung (TW); Hsin-Wei Chang, Kaohsiung (TW); Weng-Keong Tang, Kaohsiung (TW); Chia-Hui Shen, Kaohsiung (TW)

(73) Assignee: CHINA PETROCHEMICAL DEVELOPMENT CORPORATION, TAIPEI (TAIWAN), Kaohsiung (TW)

( * ) Notice: Subject to any disclaimer, the term of this patent is extended or adjusted under 35 U.S.C. 154(b) by 0 days.

(21) Appl. No.: 17/839,762

(22) Filed: Jun. 14, 2022

(65) Prior Publication Data

US 2023/0150903 A1  May 18, 2023

(30) Foreign Application Priority Data

Nov. 16, 2021  (TW) .................................. 110142565

(51) Int. Cl.
*C07C 29/20* (2006.01)

(52) U.S. Cl.
CPC .......... *C07C 29/20* (2013.01); *C07C 2601/14* (2017.05)

(58) Field of Classification Search
CPC ................................ C07C 29/19; C07C 29/20
See application file for complete search history.

(56) References Cited

U.S. PATENT DOCUMENTS

| | | | | |
|---|---|---|---|---|
| 5,874,622 A | * | 2/1999 | Breitscheidel | C07C 29/20 568/834 |
| 2014/0163117 A1 | * | 6/2014 | Rudenauer | A61Q 19/00 510/276 |
| 2018/0346398 A1 | * | 12/2018 | Liao | B01J 23/462 |

FOREIGN PATENT DOCUMENTS

| CN | 102921440 A | | 2/2013 | | |
|---|---|---|---|---|---|
| CN | 106866365 A | * | 6/2017 | ............. | C07C 29/20 |

OTHER PUBLICATIONS

Machine translation Patent No. CN106866365A, Jun. 2017, pp. 1-12 (Year: 2017).*

* cited by examiner

*Primary Examiner* — Medhanit W Bahta
(74) *Attorney, Agent, or Firm* — Sughrue Mion, PLLC

(57) ABSTRACT

The present invention provides a method for preparing 2,2-bis(4-hydroxycyclohexyl)propane, comprising: hydrogenating a reactive solution containing 2,2-bis(4-hydroxyphenyl)propane under a hydrogen atmosphere in a reactor with catalyst within a temperature range of 80-165° C. and a pressure range of 85-110 kg/cm² to prepare the 2,2-bis(4-hydroxycyclohexyl)propane. The method of present invention has an advantage of high yield properties and achieves mass production easily, thereby enhancing the value of the industrial application.

17 Claims, 2 Drawing Sheets

METHOD FOR PREPARING 2,2-BIS(4-HYDROXYCYCLOHEXYL)PROPANE

FIELD OF THE INVENTION

The present invention relates to a method for preparing 2,2-bis(4-hydroxycyclohexyl)propane, especially to a method for preparing 2,2-bis(4-hydroxycyclohexyl)propane by subjecting 2,2-bis(4-hydroxyphenyl)propane to a hydrogenation reaction under a relative milder reaction condition.

BACKGROUND OF THE INVENTION 2,2-bis(4-hydroxycyclohexyl)propane has been broadly used for preparing auxiliary chemicals including rubber aging inhibitors, plasticizers, fire retardants, antioxidants, coatings, etc. or as a raw material for preparing resins including polycarbonates, epoxy resins, polypropylene, etc. due to its thermal stability, chemical stability and weather resistance. Its application covers the fields of electronic packaging, electrical insulating materials, chemical industry, coatings and medical device industry, and it is a valuable chemical.

2,2-bis(4-hydroxycyclohexyl)propane is usually prepared by subjecting 2,2-bis(4-hydroxyphenyl)propane as the starting material to a catalytic hydrogenation reaction. However, most of the existing preparation processes are performed at a high temperature, which are at high risk and have the problem of poor reaction stability. Efforts have been done to improve the processes by increasing water content, but have very little effects.

For this reason, it is necessary to provide a method for preparing 2,2-bis(4-hydroxycyclohexyl)propane under relative milder reaction conditions to solve the problems described above occurred during the existing processes.

SUMMARY OF THE INVENTION

In order to solve the problems described above, the present invention provides a method for preparing 2,2-bis (4-hydroxycyclohexyl)propane, comprising: performing a hydrogenation reaction of a reaction solution of 2,2-bis(4-hydroxyphenyl)propane with hydrogen gas in a reactor containing a catalyst at 80-165° C. under a pressure condition of 85-110 kg/cm$^2$ to obtain 2,2-bis(4-hydroxycyclohexyl)propane.

In one embodiment of the present invention, the 2,2-bis (4-hydroxycyclohexyl)propane contains a cis/trans isomer at a content of 40-50 wt %.

In one embodiment of the present invention, the 2,2-bis (4-hydroxyphenyl)propane is present in the reaction solution at a content of 2-25 wt %.

In one embodiment of the present invention, the reaction solution further includes a solvent, for example the solvent is isopropanol.

In one embodiment of the present invention, the catalyst includes an active metal selected from at least one of Group VIII metals and a carrier bearing the active metal. In one embodiment of the present invention, the active metal can be at least one selected from the group consisting of Fe, Co, Ni, Ru, Rh, Pd, Os, Ir and Pt. In another embodiment, the active metal comprises 0.1-5 wt % of the weight of the catalyst.

In one embodiment of the present invention, the carrier is at least one selected from the group consisting of alumina, silica and carbon.

In one embodiment of the present invention, the catalyst is in the form of powders or particles; wherein the catalyst has a particle size of 2.2-2.5 mm when it is in the form of particles.

In one embodiment of the present invention, the catalyst has a specific surface area of 150-300 m$^2$/g.

In one embodiment of the present invention, the reaction solution contains water of not more than 0.5 wt %.

In one embodiment of present invention, the reactor is a continuous reactor. In another embodiment, the continuous reactor is a fixed bed reactor.

In one embodiment of present invention, the reaction solution has a liquid hourly space velocity (LHSV) of 1.12-4.48 hour$^{-1}$ when the reactor is a continuous reactor. In another embodiment of present invention, the molar ratio of the hydrogen gas to the 2,2-bis(4-hydroxyphenyl)propane is 35-100.

In one embodiment of present invention, the reactor is a batched reactor.

In another embodiment of present invention, the molar ratio of the hydrogen gas to the 2,2-bis(4-hydroxyphenyl) propane is 6-8 when the reactor is a batched reactor. In another embodiment of present invention, the catalyst is present in the reaction solution at a content of 1-2 wt %. In still another example, the hydrogenation is performed for 4-6 hrs.

In another embodiment of the present invention, the batched reactor further includes an agitator device, and the agitator device rotates at a speed of 200 to 1200 rpm.

In another embodiment of the present invention, the selectivity of the hydrogenation is 92-99%.

According to the present invention, in the presence of the catalyst and within particular condition ranges of temperature and pressure, 2,2-bis(4-hydroxycyclohexyl)propane can be prepared in a yield up to above 50% without additionally adding water, and in which the content of the cis/trans isomer of 2,2-bis(4-hydroxycyclohexyl)propane is 40-50 wt %. The method has the advantages of a high conversion rate and a high selectivity, and achieves the effects of optimized catalytic capability for the hydrogenation reaction and stabilized reaction. In addition, by operating under relative milder conditions, the preparation method of the present invention can reduce energy consumption, benefit extension the service life of the catalyst, effectively reduce overall production cost of the process, and find values in industrial applications.

BRIEF DESCRIPTION OF THE DRAWINGS

The execution modes of the present invention will be described through exemplary drawings.

DETAILED DESCRIPTION

Figure 1A:
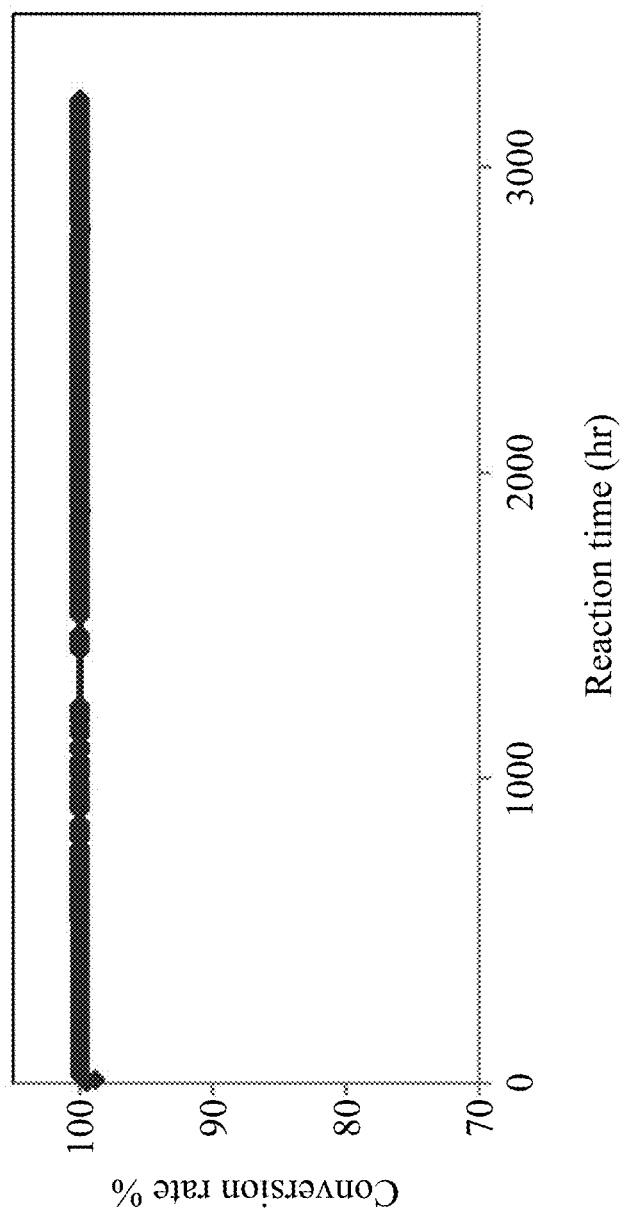
FIG. 1A is a graph recording the conversion rate of the present invention operated in a continuous process.

The execution modes of the present invention will be illustrated by following specific embodiments, anyone skilled in the art can easily realize the advantages and effects of the present invention based on the content described in the description. The present invention also can be performed or applied by other different execution modes, and the details of the present invention each can be imparted with different modifications and alternations based on different views and applications without departing from the scope described by the present invention. Furthermore, all ranges and values recited in the present invention are inclusive and combinable. Any value or point falling in the ranges recited herein, such as any integers, can be used as the lower or upper limit to derive a subrange.

According to the present invention, the present invention provides a method for preparing 2,2-bis(4-hydroxycyclohexyl)propane, comprising: performing a hydrogenation reaction of a reaction solution of 2,2-bis(4-hydroxyphenyl)propane with hydrogen gas in a reactor containing a catalyst within a temperature range of 80-165° C. under a pressure condition of 85-110 kg/cm$^2$ to obtain 2,2-bis(4-hydroxycyclohexyl)propane.

In other embodiments, the hydrogenation reaction can be performed at a temperature of 85, 90, 95, 100, 105, 110, 115, 120, 125, 130, 135, 140, 150, 155 or 160° C., and under a pressure of 90, 95, 100 or 105 kg/cm$^2$, but not limited thereto.

Herein, the reaction solution is a homogeneous, stable dispersing system formed by mixing two or more materials, wherein one of the materials is the reactant 2,2-bis(4-hydroxyphenyl)propane. In one embodiment, the reactant 2,2-bis(4-hydroxyphenyl)propane is present in the reaction solution at a content of 2-25 wt %.

In another embodiment, the reaction solution further includes a solvent which is preferably alcohol solvent. In examples of the present invention, the alcohol solvent is isopropanol.

Herein, the hydrogenation reaction is performed under the action of the catalyst to add a hydrogen molecule to an unsaturated group in a reactant, thus the hydrogenation capability of the catalyst and the reaction conditions are critical to the stability of the hydrogenation reaction.

The catalyst of the present invention is of a type of noble metals supported catalyst, comprises active metal(s) having hydrogenation function and a carrier supporting the active metal(s), can be in the form of powders or particles, and can be characterized in a porous catalyst, but not limited thereto.

In one embodiment, the catalyst has a particle size of 2.2-2.5 mm when it is in the form of particles.

In another embodiment, the catalyst has a specific surface area of 150-300 m$^2$/g.

In preparation, the catalyst is obtained by bearing the active metal on the carrier firstly, and then subjecting to washing, water removal and calcining treatments. In order to accelerate progress of the hydrogenation, the active metal is allowed to distribute preferentially on the outer surface of the catalyst, in other words, the active metal on the surface layer of the catalyst has a concentration higher than that in the core. Thus, the overall load of the active metal and the production cost are reduced.

In one embodiment, the active metal is at least one selected from Group VIII metals, for example, the active metal can be at least one selected from the group consisting of Fe, Co, Ni, Ru, Rh, Pd, Os, Ir and Pt. In addition, in examples of the present invention, the catalyst is free of Pb. In some embodiments of the present invention, the active metal comprises 0.1-5 wt % of the weight of the catalyst.

In one embodiment, the active metal is at least one selected from Ru and Rh. For example, the active metal is selected from Ru, Rh or contains both of Ru and Rh. Also, in the embodiment that the active metal contains Ru and Rh, the content of Ru can be larger than that of Rh.

In one embodiment, the carrier is at least one selected from the group consisting of alumina, silica and carbon.

Herein, the 2,2-bis(4-hydroxyphenyl)propane utilizes preferably 2,2-bis(4-hydroxyphenyl)propane with a purity more than 99%.

In the preparation method of the present invention, the hydrogenation reaction is performed by selecting the catalyst described above and within particular condition ranges of temperature and pressure to provide a stable reaction state. Therefore, the reaction solution used in the preparation method of the present invention contains water of not more than 0.5 wt % and needs no additionally adding water to the reaction system, and effects of optimized hydrogenation reaction and effectively enhanced yield up to above 50% can be achieved by using a reaction solution with a water content not more than 0.5 wt %.

Since 2,2-bis(4-hydroxycyclohexyl)propane has two ring planes in the structure and each of the two ring planes has combinations of cis- and trans-configurations due to hindered free rotations of the substituents on the rings. In the preparation method of the present invention, the 2,2-bis(4-hydroxycyclohexyl)propane prepared contains a cis/trans isomer at a content of 40-50 wt %.

In addition, the preparation method of the present invention can be conducted in a batched or a continuous process.

In a continuous process, the reactor is a continuous reactor operated by continuous feeding, continuous reaction and continuous unloading, and the continuous reactor includes a fixed bed reactor, a moving bed reactor, a fluidized bed reactor or a continuous stirring tank reactor. In one embodiment of the present invention, the continuous reactor is particularly preferably a fixed bed reactor.

The fixed bed reactor, also called packed bed reactor, is a reactor packed with a solid catalyst or a solid reactant to realize a multi-phase reaction process. In a fixed bed reactor, there is a bed layer which is stacked by the solid catalyst or solid reactant and is fixed during the reaction to allow a fluid to pass through the bed layer for reacting. Such a device is characterized in low wear loss of the catalyst, and a relative higher yield can be achieved by using a small amount of catalyst, therefore, it is beneficial for reaching a higher selectivity and a higher conversion rate.

In the present invention, the fixed bed reactor can be selected based on its real requirement for heat transfer and the reaction rate, for example, trickle bed reactor, thermal isolation fixed bed reactor, heat exchange fixed bed reactor, axially flowing fixed bed reactor or radially flowing fixed bed reactor, but not limited thereto.

Since the continuous reactor of the present invention is classified to a heterogeneous reaction system, the flow rate of the reactant steam could affect flow layer thickness on the catalyst and the mass delivery between reactants. In one embodiment, the reaction solution has a liquid hourly space velocity (LHSV) of 1.12-4.48 hour$^{-1}$.

In other embodiments, the reaction solution can have a liquid hourly space velocity of 1.15, 1.2, 1.4, 1.6, 1.8, 2, 2.2, 2.4, 2.6, 2.8, 3.0, 3.2, 3.4, 3.6, 3.8, 4.0, 4.2 or 4.4 hour$^{-1}$, but not limited thereto.

In a continuous process, the molar ratio of the hydrogen gas to the 2,2-bis(4-hydroxyphenyl)propane can be referred as "hydrogen to oil ratio" or "excess hydrogen to oil ratio". In another embodiment, the molar ratio of the hydrogen gas to the 2,2-bis(4-hydroxyphenyl)propane is 35-100.

In other embodiments, the molar ratio of the hydrogen gas to the 2,2-bis(4-hydroxyphenyl)propane can be 40, 45, 50, 55, 60, 65, 70, 75, 80, 85, 90 or 95, but not limited thereto.

In addition, the catalyst used in the fixed bed reactor described above can be filled in the form of particles, webs, honeycombs or fibers, wherein the catalyst filled in the form of particles is preferred. In another embodiment, the catalyst can also be combined with an inert material, to regulate the pressure drop during the reactant flows through the bed layer containing the catalyst, to control the time period when the reactants contact the catalyst, and to pack the catalyst uniformly and dispersedly in the reactor, therefore, the thermal energy generated during the reaction process is dissipated rapidly which contributes to temperature control during the reaction process.

In a batched process, the reactor is a batched reactor operated in such a mode that the reactor is loaded in batches to perform the reaction and unloaded when the reaction is completed or performed for a predetermined period. In embodiments of the present invention, the batched reactor further includes an agitator device and wherein the batched reactor is a stirred tank reactor, and the agitator device rotates at a speed of 200-1200 rpm. Wherein the agitator device can be selected from propeller type agitator, turbine agitator, paddle agitator, anchor agitator, folding blade agitator, side agitator, screw agitator, magnetic heating agitator, or helical ribbon agitator.

In another embodiment, the molar ratio of the hydrogen gas to the 2,2-bis(4-hydroxyphenyl)propane is 6-8 when the reactor is a batched reactor.

In another embodiment, the catalyst is present in the reaction solution at a content of 1-2 wt % when the reactor is a batched reactor.

In still another embodiment, when the reactor is a batched reactor, the hydrogenation is performed for 4-6 hrs.

By the reaction conditions setting described above, the selectivity of the hydrogenation reaction in the preparation method of the present invention is 92-99%. In preferred embodiments, the selectivity of the hydrogenation reaction in the preparation method of the present invention can be up to 95-99%.

The features and effects of the present invention will be described in detail through examples and comparative examples which are not considered to restrict the scope of the present invention.

The conversion rates and selectivities recorded in the specification are defined as following:

Conversion rate=(the initial concentration of 2,2-bis(4-hydroxyphenyl)propane−the residual concentration of 2,2-bis(4-hydroxyphenyl)propane)/the initial concentration of 2,2-bis(4-hydroxyphenyl)propane*100%

Selectivity=concentration of 2,2-bis(4-hydroxycyclohexyl)propane in the product/the consumed concentration of 2,2-bis(4-hydroxyphenyl)propane*100%

Comparative Example 1

9 g of the ground catalyst was taken and filled in a tank reactor having a volume of 1 L and a blade stirrer, wherein the catalyst contained active metals of 1.5 wt % ruthenium (Ru) and carrier alumina ($Al_2O_3$), had the physical properties prior to grinding as shown in Table 1 and the average particle size of 32.5 μm after grinding. By controlling the conditions of the reactor at a temperature of 170° C. and a pressure of 80 kg/$cm^2$, the reaction solution containing 2,2-bis(4-hydroxyphenyl)propane (BPA) was subjected to a batched hydrogenation reaction with hydrogen gas to obtain 2,2-bis(4-hydroxycyclohexyl)propane as the product; wherein the solvent of the reaction solution was isopropanol, the reaction solution contained 2,2-bis(4-hydroxyphenyl) propane at a content of 10 wt % and the catalyst at a content of 1.5 wt %, the stirrer rotated at a speed of 300 rpm, and the molar ratio of the hydrogen gas to the 2,2-bis(4-hydroxyphenyl)propane was 5.5. A stable reaction was achieved after reacting for 4 hrs, the product was analyzed through a Shimadzu GC-2010 Plus gas chromatography, and the conversion rate and selectivity were recorded in Table 2.

TABLE 1

| Catalyst characteristics | Unit | Value |
| --- | --- | --- |
| Particle size | mm | 2.2-2.5 |
| Density | g/l | 550 |
| Crushing strength | N | >100 |
| Specific surface area | $m^2$/g | 260 |

Comparative Example 2

The same preparation method as Comparative Example 1 was performed to prepare 2,2-bis(4-hydroxycyclohexyl)propane as the product, except that the composition and ratios of the active metals of the catalyst were altered as shown in Table 2, and the conversion rate and selectivity were recorded in Table 2.

Example 1

The same preparation method as Comparative Example 1 was performed to prepare 2,2-bis(4-hydroxycyclohexyl)propane as the product, except that the pressure and temperature for performing the hydrogenation reaction, the molar ratio of the hydrogen gas to the 2,2-bis(4-hydroxyphenyl)propane, and the composition and ratios of the active metals of the catalyst were altered as shown in Table 2, and the conversion rate and selectivity were recorded in Table 2.

Example 2

The same preparation method as Example 1 was performed to prepare 2,2-bis(4-hydroxycyclohexyl)propane as the product, except that the temperature set for performing the hydrogenation reaction and the molar ratio of the hydrogen gas to the 2,2-bis(4-hydroxyphenyl)propane were altered as shown in Table 2, and the conversion rate and selectivity were recorded in Table 2.

Example 3

The same preparation method as Example 2 was performed to prepare 2,2-bis(4-hydroxycyclohexyl)propane as the product, except that the pressure set for performing the hydrogenation reaction and the molar ratio of the hydrogen gas to the 2,2-bis(4-hydroxyphenyl)propane were altered as shown in Table 2, wherein the 2,2-bis(4-hydroxycyclohexyl)propane prepared contained a cis/trans isomer at a content of 50 wt %, a cis/cis isomer at a content of 26 wt %, and a trans/trans isomer at a content of 24 wt %, and the conversion rate and selectivity were recorded in Table 2.

Example 4

The same preparation method as Example 3 was performed to prepare 2,2-bis(4-hydroxycyclohexyl)propane as the product, except that the content of 2,2-bis(4-hydroxyphenyl)propane in the reaction solution and the molar ratio of the hydrogen gas to the 2,2-bis(4-hydroxyphenyl)propane were altered as shown in Table 2, and the conversion rate and selectivity were recorded in Table 2.

TABLE 2

| | Catalyst | | | Batched Reaction Conditions | | | Reaction | |
|---|---|---|---|---|---|---|---|---|
| | Active metal | Carrier | Active metal Content (wt %) | Pressure (kg/cm$^2$) | Temperature (° C.) | Molar ratio of hydrogen gas/BPA | solution Concentration of BPA (wt %) | Conversion rate (%) | Selectivity (%) |
| COM. EX. 1 | Ru | Al$_2$O$_3$ | 1.5 | 80 | 170 | 5.5 | 10 | 99.47 | 79.09 |
| COM. EX. 2 | | | 2 | | | | | 99.95 | 89.03 |
| Ex. 1 | Ru/Rh | | 2 wt % Ru, 0.3 wt % Rh | 85 | 165 | 6 | | 99.96 | 93.45 |
| Ex. 2 | | | | | 110 | 7 | | 99.96 | 98.45 |
| Ex. 3 | | | | 100 | | 7.5 | | 100 | 98.89 |
| Ex. 4 | | | | | | 8 | 20 | 100 | 98.75 |

Comparative Example 3

60 g of the catalyst was taken and filled in a fixed bed reactor, wherein the catalyst contained active metals of 2 wt % ruthenium (Ru) and 0.3 wt % rhodium (Rh) and carrier alumina (Al$_2$O$_3$) and had the physical properties as shown in Table 1. A continuous hydrogenation reaction was performed by controlling the flow rate of the reaction solution and hydrogen gas fed into the reactor and controlling the conditions of the reactor at a temperature of 170° C. and a pressure of 80 kg/cm$^2$, to obtain 2,2-bis(4-hydroxycyclohexyl)propane as the product; wherein the reaction solution contained the reactant 2,2-bis(4-hydroxyphenyl)propane and the solvent isopropanol, and the 2,2-bis(4-hydroxyphenyl)propane was present in the reaction solution at a content of 10 wt %; the reaction solution has a liquid hourly space velocity (LHSV) of 1.12 hour$^{-1}$, and the molar ratio of the hydrogen gas to the 2,2-bis(4-hydroxyphenyl)propane (BPA) was 100. A stable reaction was achieved after reacting for 8 hrs, the product was analyzed through a Shimadzu GC-2010 Plus gas chromatography, and the conversion rate and selectivity were recorded in Table 3.

Comparative Example 4

The same preparation method as Comparative Example 3 was performed to prepare 2,2-bis(4-hydroxycyclohexyl)propane as the product, except that the molar ratio of the hydrogen gas to the 2,2-bis(4-hydroxyphenyl)propane were altered as shown in Table 3, and the conversion rate and selectivity were recorded in Table 3.

Example 5

The same preparation method as Comparative Example 3 was performed to prepare 2,2-bis(4-hydroxycyclohexyl)propane as the product, except that the molar ratio of the hydrogen gas to the 2,2-bis(4-hydroxyphenyl)propane and the temperature and pressure conditions for performing the hydrogenation reaction were altered as shown in Table 3, and the conversion rate and selectivity were recorded in Table 3.

Example 6

The same preparation method as Example 5 was performed to prepare 2,2-bis(4-hydroxycyclohexyl)propane as the product, except that the molar ratio of the hydrogen gas to the 2,2-bis(4-hydroxyphenyl)propane were altered as shown in Table 3, and the conversion rate and selectivity were recorded in Table 3.

Example 7

The same preparation method as Example 6 was performed to prepare 2,2-bis(4-hydroxycyclohexyl)propane as the product, except that the molar ratio of the hydrogen gas to the 2,2-bis(4-hydroxyphenyl)propane and the pressure condition for performing the hydrogenation reaction were altered as shown in Table 3, and the conversion rate and selectivity were recorded in Table 3.

Example 8

Figure 1B:
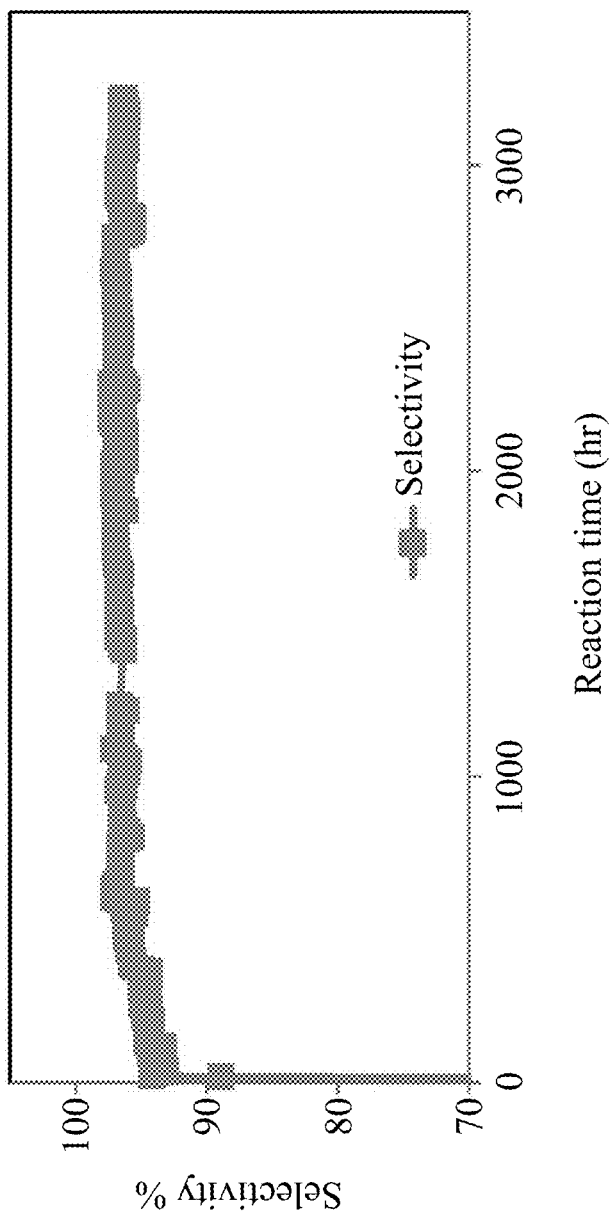
FIG. 1B is a graph recording the selectivity of the present invention operated in a continuous process.

The same preparation method as Example 7 was performed to prepare 2,2-bis(4-hydroxycyclohexyl)propane as the product, except that the pressure condition for performing the hydrogenation reaction were altered as shown in Table 3, and the conversion rate and selectivity were recorded in Table 3 and FIGS. 1A and 1B.

It can be seen from FIGS. 1A and 1B, the catalyst of the present invention still exhibits a stable catalytic activity after a continuous operation for 3222 hours, suggesting that the catalyst in the preparation method of the present invention has good stability and catalytic capability, thereby allowing the process to maintain excellent conversion rate and selectivity after operation for a lone period.

Examples 9 to 12

The same preparation method as Example 8 was performed to prepare 2,2-bis(4-hydroxycyclohexyl)propane as the product, except that the liquid hourly space velocity of the reaction solution were altered as shown in Table 3, and the conversion rate and selectivity were recorded in Table 3.

TABLE 3

| | \<colspan=3\>Continuous Reaction Conditions | | | |
|---|---|---|---|---|---|
| | Pressure (kg/cm$^2$) | Temperature (° C.) | LHSV (hr$^{-1}$) | Molar ratio of hydrogen gas/BPA | Conversion Rate (%) | Selectivity (%) |
| COM. EX. 3 | 80 | 170 | 1.12 | 100 | 99.999 | 76.76 |
| COM. EX. 4 | 100 | 110 | | 53 | 99.999 | 82.42 |
| Ex. 5 | | | | 40 | 99.99 | 96.42 |
| Ex. 6 | | | | 72 | 100 | 96.71 |
| Ex. 7 | 85 | | | 53 | 99.882 | 92.59 |
| Ex. 8 | 100 | | | | 100 | 96.78 |
| Ex. 9 | | | 1.49 | | 100 | 96.73 |
| Ex. 10 | | | 2.24 | | 100 | 96.70 |
| Ex. 11 | | | 2.65 | | 99.996 | 96.53 |
| Ex. 12 | | | 4.48 | | 99.997 | 95.48 |

In conclusion, the method for preparing 2,2-bis(4-hydroxycyclohexyl)propane of the present invention is performed in the presence of the catalyst and within particular condition ranges of temperature and pressure to prepare 2,2-bis(4-hydroxycyclohexyl)propane in a yield up to above 50% without additionally adding water, and in which the content of the cis/trans isomer of 2,2-bis(4-hydroxycyclohexyl)propane is 40-50 wt %. The method has the advantages of a high conversion rate and a high selectivity, and achieves the effects of optimized catalytic capability for the hydrogenation reaction and stabilized reaction. In addition, by operating under relative milder conditions, the preparation method of the present invention can reduce energy consumption, benefit extension the service life of the catalyst in relative to that of 1500 hours of the prior arts, effectively reduce overall production cost of the process, and find values in industrial applications.

The above examples are used for illustration only but not for limiting the present invention. Modifications and alternations can be made to above examples by anyone skilled in the art without departing from the spirit and scope of the present invention. Therefore, the range claimed by the present invention should be defined by attached claims and should be encompassed within the disclosure of the present invention as long as that doesn't influence effects and purposes of the present invention.

The invention claimed is:

1. A method for preparing 2,2-bis(4-hydroxycyclohexyl) propane, comprising:
performing a hydrogenation reaction of a reaction solution of 2,2-bis(4-hydroxyphenyl)propane with hydrogen gas in a reactor containing a catalyst at 80-165° C. under a pressure condition of 85-110 kg/cm$^2$ to obtain 2,2-bis(4-hydroxycyclohexyl)propane,
wherein the reaction solution contains water of not more than 0.5 wt %,
wherein the catalyst includes an active metal and a carrier bearing the active metal, and wherein the active metal is at least one selected from the group consisting of Fe, Co, Ni, Ru, Rh, Pd, Os, Ir and Pt,
wherein the catalyst is in the form of powders or particles, and
wherein the catalyst has a specific surface area of 150-300 m$^2$/g.

2. The preparation method of claim 1, wherein the 2,2-bis(4-hydroxycyclohexyl)propane contains a cis/trans isomer at a content of 40-50 wt %.

3. The preparation method of claim 1, wherein the 2,2-bis(4-hydroxyphenyl)propane is present in the reaction solution at a content of 2-25 wt %.

4. The preparation method of claim 1, wherein the reaction solution further contains an alcohol solvent.

5. The preparation method of claim 1, wherein the active metal comprises 0.1-5 wt % of the weight of the catalyst.

6. The preparation method of claim 1, wherein the carrier is at least one selected from the group consisting of alumina, silica and carbon.

7. The preparation method of claim 1, wherein the catalyst is in the form of particles and has a particle size of 2.2-2.5 mm.

8. The preparation method of claim 1, wherein the reactor is a continuous reactor.

9. The preparation method of claim 8, wherein the reaction solution has a liquid hourly space velocity of 1.12-4.48 hour$^{-1}$.

10. The preparation method of claim 8, wherein the molar ratio of the hydrogen gas to the 2,2-bis(4-hydroxyphenyl) propane is 35-100.

11. The preparation method of claim 1, wherein the reactor is a fixed bed reactor.

12. The preparation method of claim 1, wherein the reactor is a batched reactor.

13. The preparation method of claim 12, wherein the molar ratio of the hydrogen gas to the 2,2-bis(4-hydroxyphenyl)propane is 6-8.

14. The preparation method of claim 12, wherein the catalyst is present in the reaction solution at a content of 1-2 wt %.

15. The preparation method of claim 12, wherein the batched reactor further includes an agitator device and the agitator device rotates at a speed of 200-1200 rpm.

16. The preparation method of claim 12, wherein the hydrogenation is performed for 4-6 hrs.

17. The preparation method of claim 1, wherein the selectivity of the hydrogenation reaction is 92-99%.

* * * * *